US00PP09721P

United States Patent [19]

Ilsink

[11] Patent Number: Plant 9,721

[45] Date of Patent: Dec. 3, 1996

[54] FLORIBUNDA ROSE PLANT VARIETY NAMED 'INTERTYN'

[75] Inventor: G. P. Ilsink, Doorn, Netherlands

[73] Assignee: DeVor Nurseries, Inc., Watsonville, Calif.

[21] Appl. No.: 596,710

[22] Filed: Feb. 5, 1996

[51] Int. Cl.[6] ..... A01H 5/00

[52] U.S. Cl. ..... Plt./25

[58] Field of Search ..... Plt./22, 25, 26

*Primary Examiner*—Howard J. Locker

*Attorney, Agent, or Firm*—Christie, Parker & Hale, LLP

[57] ABSTRACT

A new variety of floribunda rose plant producing salmon colored flowers.

1 Drawing Sheet

SUMMARY OF THE INVENTION

The present invention relates to a new and distinct variety of rose of the floribunda rose class which was originated by my crossing as seed and pollen parents two unnamed, unpatented, undistributed, proprietary seedlings of my creation. The varietal denomination of this new rose is 'Intertyn'.

Among the novel characteristics possessed by this new variety which distinguishes it from its parents are its ability to produce commercially desirable sprays of attractive salmon colored flowers for the cut flower market.

Asexual reproduction by budding and grafting of the new variety as performed in Watsonville, Calif., shows that the foregoing and other distingishing characteristics come true to form and are established and transmitted through succeeding propagations.

BRIEF DESCRIPTION OF ILLUSTRATION

The accompanying illustration shows typical specimens of the flowers and vegetative growth of the new variety depicted in color as nearly true as it is reasonably possible to make the same in a color illustration of this character. Phenotypic expression, including colors, may vary depending upon growing conditions, such as climate, soil, and environmental conditions.

DESCRIPTION OF THE NEW VARIETY

The following is a detailed description of my new variety, with color terminology in accordance with The Royal Horticultural Society Color Chart (R.H.S.C.C.). The terminology used in color description herein refers to plate numbers in the aforementioned color chart. Where general terms such as average, normal, ordinary, medium, etc. are used, the characteristics so described are not considered distinguishing.

Parentage: Seedling.

*Seed parent.*—Unnamed seedling.

*Pollen parent.*—Unnamed seedling.

Class: Floribunda.

The following information is from observation made of specimens grown under glass in Watsonville, Calif. in the month of November.

FLOWER

Blooming habit: Continuous.

A. Bud:

(1) *Size.*—Small.

(2) *Form.*—Globose.

(3) *Color.*—As sepals divide, bud color is near 35C.

(4) *Sepals.*—Broadly elliptical with acute tip.

(5) *Peduncle.*—Length: About 5 to 13 cm. Aspect: Many very small prickles. Strength: Erect, sturdy. Color: Near 138B.

(6) *Bracts.*—0 to 2 per bud. Color — near 136B. Form — broadly lanceolate with caudate apex. Location in relation to flower — about 4 to 6 cm below calyx of bud.

B. Bloom:

(1) *Size.*–About 5 to 6 cm.

(2) *Borne.*—Blooms borne in sprays of 3 to 9 blooms.

(3) *Form.*—Cupped.

(4) *Petalage.*—Number of petals under normal conditions — about 35 to 42.

(5) *Color* (⅓ to ½ *open*).—Outer petals — Top surface near 37B. — Undersurface near 37C. Inner petals — Top surface near 37B. — Undersurface near 37C. Base of petals — Near 157D. General tonality from a distance — Salmon.

(6) *Color* (*fully open*).—Outer petals — Top surface undersurface near 39C. Inner petals — Top surface and undersurface near 39C. Base of petals — near 157D. General tonality from a distance — salmon.

(7) *Color change.*—Petal top and undersurface — lightens. Base of petals — lightens. General tonality at a distance — salmon.

C. Petals:

(1) *Texture.*—Smooth.

(2) *Appearance.*—Inside satiny; outside slightly satiny.

(3) *Form.*—Elliptic with notch.

(4) *Arrangement.*—Imbricated.

(5) *Petaloids in center.*—None.

(6) *Persistence.*—Petals drop off cleanly.

(7) *Fragrance.*—None.

(8) *Lasting quality.*—About 12 to 14 days on plant and about 8 to 10 days in vase after cutting.

REPRODUCTIVE ORGANS

A. Stamens, filaments and anthers:

*Arrangement.*—Slightly retrorse.

*Filaments.*—Color near 162D.

*Anthers.*—Color near 22A.

*Pollen.*—Color near 22A.

B. Styles: Bunched evenly together.

*Stigma.*—Color — near 160C.

PLANT

A. Form: Upright.

B. Growth: Vigorous; about 75–100 cm.

C. Foliage:

(1) *Size.*—Small.

(2) Quantity.—Abundant.

(3) *Color.*—New foliage: Upper side near 136B. Underside near 137C. Old foliage: Upper side near 137B. Underside — near 137B.

(4) *Shape.*—Ovate.

(5) *Texture.*—Upper side is smooth, leathery and underside is slightly leathery.

(6) *Edge.*—Serrated.

(7) *Serration.*—Serrate.

(8) *Petiole color.*—Top surface — near 148A. Underside near 148B.

(9) *Stipules.*—Adnate.

(10) *Auricle.*—Facing outwards, long.

(11) *Rachis.*—Smooth underneath.

(12) *Resistance to disease.*—Very resistant to mildew, rust and black spot.

D. Wood:

(1) *New wood.*—Bark — some prickles.

(2) *Old wood.*—Bark — some prickles.

(3) *Flower stem length from last cutting.*—About 65 cm on average.

E. Thorns:

*Quantity on basal canes.*—Very few.

*Quantity on laterals.*—None.

*Position.*—Irregular.

*Prickles.*—Small prickles on peduncle.

F. Winter hardiness: Completely winter hardy in Watonsville, Calif.

I claim:

1. A new and distinct variety of rose plant of the floribunda rose class, substantially as shown and described.

* * * * *

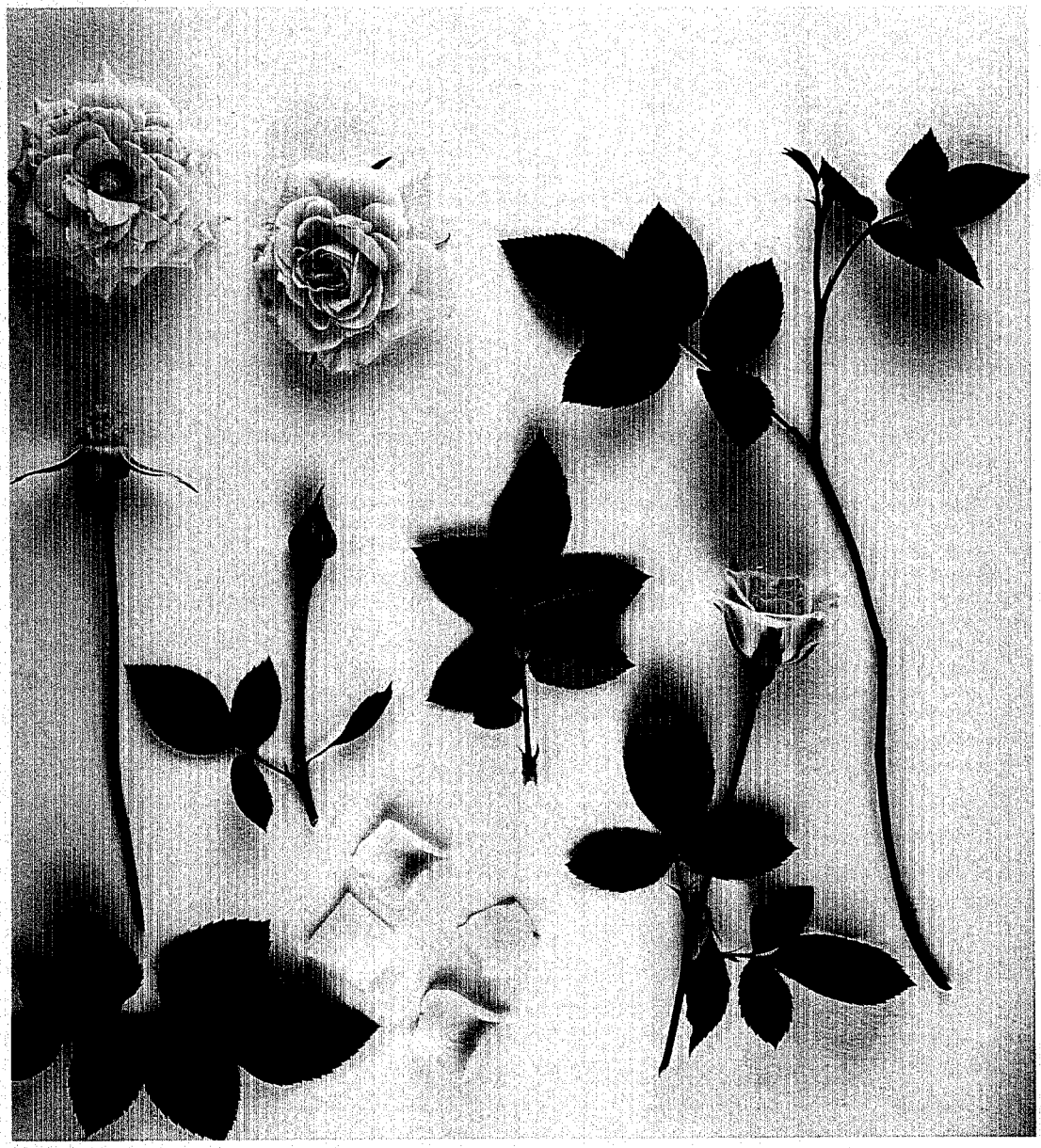

UNITED STATES PATENT AND TRADEMARK OFFICE

CERTIFICATE OF CORRECTION

PATENT NO. : Plant 9,721
DATED : December 3, 1996
INVENTOR(S) : G. P. Ilsink

It is certified that error appears in the above-indentified patent and that said Letters Patent is hereby corrected as shown below:

Column 1, line 15, change "distingishing" to -- distinguishing --.
Column 1, line 43, change "observation" to -- observations --.
Column 2, line 22, after "Top surface" insert -- and --.

Signed and Sealed this
Seventh Day of October, 1997

*Attest:*

*Attesting Officer*

Bruce Lehman

BRUCE LEHMAN

*Commissioner of Patents and Trademarks*